US010031047B2

(12) United States Patent
Oba et al.

(10) Patent No.: US 10,031,047 B2
(45) Date of Patent: Jul. 24, 2018

(54) GAS SENSOR

(71) Applicant: NGK Spark Plug Co., LTD., Nagoya (JP)

(72) Inventors: Takehiro Oba, Konan (JP); Shogo Nagata, Komaki (JP); Shunya Mihara, Komaki (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 0 days.

(21) Appl. No.: 15/472,520

(22) Filed: Mar. 29, 2017

(65) Prior Publication Data

US 2017/0307478 A1    Oct. 26, 2017

(30) Foreign Application Priority Data

Apr. 20, 2016  (JP) ................................ 2016-084804

(51) Int. Cl.
*G01M 15/10* (2006.01)

(52) U.S. Cl.
CPC ................................ *G01M 15/104* (2013.01)

(58) Field of Classification Search
CPC ............ G01M 15/104; G01N 27/4062; G01N 27/4065
See application file for complete search history.

(56) References Cited

U.S. PATENT DOCUMENTS

| 4,857,164 | A  | * | 8/1989  | Kodachi | ............ | G01N 27/4065 |
|           |    |   |         |         |              | 204/406      |
| 7,104,685 | B2 | * | 9/2006  | Hanzawa | ................. | G01K 1/18    |
|           |    |   |         |         |              | 374/144      |
| 8,586,394 | B2 | * | 11/2013 | Fosaaen  | ............. | G01N 27/4067 |
|           |    |   |         |         |              | 205/784      |
| 9,151,728 | B2 | * | 10/2015 | Kato     | .................. | G01N 27/4062 |
| 9,335,311 | B2 | * | 5/2016  | Yonezu   | .............. | G01N 33/0009 |
| 9,482,637 | B2 | * | 11/2016 | Oba      | ....... | G01N 27/407  |
| 2002/0017127 | A1 | * | 2/2002 | Nakano   | .............. | G01N 27/4062 |
|           |    |   |         |         |              | 73/31.05     |

(Continued)

FOREIGN PATENT DOCUMENTS

JP        2002-323470 A     11/2002
JP        2007121118 A   *  5/2007

OTHER PUBLICATIONS

English Description of JP2007121118. Obtained Sep. 18, 2017.*

*Primary Examiner* — Harshad R Patel
*Assistant Examiner* — Punam Roy
(74) *Attorney, Agent, or Firm* — Leason Ellis LLP

(57) ABSTRACT

A metal terminal of a gas sensor includes a forward terminal member and a rear terminal member. The forward terminal member is made of a material superior in heat resistance to and greater in "0.2% yield strength" than a material of the rear terminal member. The forward terminal member has heat resistance suitable for a portion which comes into contact with a high-temperature detection element and is larger in an elastic deformation region than the rear terminal member, thereby providing good contact with the detection element and thus facilitating maintenance of electrical contact with the detection element. The rear terminal member is unlikely to have springback at a signal-wire connection portion to be connected to a lead wire, thereby facilitating maintenance of electrical connection with the lead wire.

11 Claims, 11 Drawing Sheets

(56) References Cited

U.S. PATENT DOCUMENTS

| | | | |
|---|---|---|---|
| 2005/0040039 A1* | 2/2005 | Kojima | G01N 27/4071 204/424 |
| 2006/0101900 A1* | 5/2006 | Nishio | G01N 27/4062 73/31.05 |
| 2009/0223818 A1* | 9/2009 | Matsui | G01N 27/4062 204/412 |
| 2011/0259084 A1* | 10/2011 | Atsumi | G01N 27/4067 73/31.05 |
| 2014/0144777 A1* | 5/2014 | Isomura | G01N 27/4067 204/408 |
| 2014/0298931 A1* | 10/2014 | Oba | G01N 27/4062 73/866.5 |
| 2015/0330938 A1* | 11/2015 | Henson | G01N 27/4114 205/783 |
| 2017/0138796 A1* | 5/2017 | Yoshida | G01K 1/08 |
| 2017/0212090 A1* | 7/2017 | Kume | G01N 33/0036 |
| 2017/0241844 A1* | 8/2017 | Oya | G01K 7/00 |
| 2017/0307560 A1* | 10/2017 | Oba | G01N 27/4073 |
| 2017/0370877 A1* | 12/2017 | Mihara | G01N 33/0037 |
| 2018/0003669 A1* | 1/2018 | Nagata | G01N 27/4073 |
| 2018/0011049 A1* | 1/2018 | Oba | G01N 27/4062 |

* cited by examiner

US 10,031,047 B2

GAS SENSOR

This application claims the benefit of Japanese Patent Application No. 2016-084804, filed Apr. 20, 2016, which is incorporated herein in its entirety by reference.

FIELD OF THE INVENTION

The present invention relates to a gas sensor which includes a sensor element having a plurality of electrode terminal portions, metal terminals electrically connected to the respective electrode terminal portions of the sensor element, and signal wires electrically connected to the respective metal terminals and forming signal paths for outputting detection signals to external equipment.

BACKGROUND OF THE INVENTION

A known gas sensor detects a particular component (target gas) contained in gas to be measured. The gas sensor includes, for example, a sensor element having electrode terminal portions, metal terminals electrically connected to the respective electrode terminal portions of the sensor element, and signal wires electrically connected to the respective metal terminals and forming signal paths for outputting detection signals to external equipment. The electrode terminal portions are provided so as to output a detection signal indicative of results of detection of the target gas to external equipment or to receive current or voltage from the outside.

The metal terminal provided in such a gas sensor is not limited to one formed of a single member, but a metal terminal composed of two members connected together is proposed. Specifically, a proposed metal terminal has a structure in which a male connector terminal to be connected to the sensor element, and a female connector terminal to be connected to a signal wire (lead wire) are connected together (see Japanese Patent Application Laid-Open (kokai) No. 2002-323470).

Problem to be Solved by the Invention

However, since, in the above conventional gas sensor, the two members (the male connector terminal and the female connector terminal) used to form the metal terminal are formed of the same material, the gas sensor may fail to simultaneously achieve sufficient heat resistance and maintenance of electrical connection in a certain application thereof.

For example, in the case of application of the gas sensor to measurement of high-temperature gas, the sensor element of the gas sensor is exposed to the high-temperature gas to be measured; accordingly, since a forward end portion of the metal terminal in contact with the sensor element is also exposed to high temperature, the forward end portion of the metal terminal must have heat resistance. Also, the forward end portion of the metal terminal in contact with the sensor element (particularly, an electrode terminal portion) must have a large elastic deformation region in order to maintain a good electrical connection with the electrode terminal portion.

Meanwhile, a rear end portion of the metal terminal must have an undeformable characteristic in order to maintain an electrical connection with the signal wire (lead wire).

However, since the design of the above conventional gas sensor does not take into consideration the above requirements for the metal terminal, the gas sensor has encountered difficulty in simultaneously achieving sufficient heat resistance of the forward end portion of the metal terminal, maintenance of electrical connection between the metal terminal and the sensor element (electrode terminal portion), and maintenance of electrical connection between the metal terminal and the signal wire (lead wire).

In view of the above problem, an object of the present invention is to provide a gas sensor which can simultaneously achieve sufficient heat resistance of a forward end portion of a metal terminal, maintenance of electrical connection between the metal terminal and a sensor element (electrode terminal portion), and maintenance of electrical connection between the metal terminal and a lead wire.

SUMMARY OF THE INVENTION

Means for Solving the Problem

A gas sensor according to one aspect of the present invention comprises a sensor element, a metal terminal, and a signal wire. The metal terminal comprises a forward terminal member and a rear terminal member.

The sensor element has at least one electrode terminal portion. The electrode terminal portion is provided so as to output a detection signal indicative of the result of detection of a target gas to external equipment or to receive current or voltage from the outside. The metal terminal is electrically connected to the electrode terminal portion of the sensor element. The signal wire is electrically connected to the metal terminal and forms a signal path for outputting the detection signal to the external equipment.

The forward terminal member is in contact with the electrode terminal portion and has a female connection portion. The rear terminal member is connected to the signal wire and has a male connection portion connected to the female connection portion. The forward terminal member and the rear terminal member are configured so that the electrode terminal portion is electrically connected to the signal wire while the female connection portion and the male connection portion are connected together.

The forward terminal member is made of a material superior in heat resistance to and greater in 0.2% yield strength than a material of the rear terminal member.

Since the metal terminal comprises the forward terminal member and the rear terminal member made of materials having different characteristics, respectively, a portion of the metal terminal in contact with the sensor element and a portion of the metal terminal connected to the signal wire differ in characteristics.

Since the forward terminal member is made of a material superior in heat resistance to and greater in "0.2% yield strength" than a material used to form the rear terminal member, the forward terminal member has heat resistance suitable for a portion which comes into contact with the high-temperature sensor element and is larger in elastic deformation region (less susceptible to plastic deformation) than the rear terminal member, thereby providing good contact with the sensor element and facilitating maintenance of electrical contact with the sensor element. Since the female connection portion can be designed more easily to reduce rigidity than can the male connection portion, by means of not only employing different materials for the female connection portion and the male connection portion, but also providing the forward terminal member with the female connection portion, the forward terminal member provides improved contact with the sensor element and facilitates maintenance of electrical contact with the sensor element.

Since the rear terminal member is made of a material having "0.2% yield strength" equivalent to or smaller than that of a material of the forward terminal member; i.e., made of a plastically deformable material, in connecting the rear terminal member to the signal wire by deforming (e.g., crimping) a connection portion to be connected to the signal wire, springback is unlikely to occur at the connection portion. Since such a rear terminal member provides firm connection between the connection portion and the signal wire, the rear terminal member facilitates maintenance of electrical connection with the signal wire.

Thus, the gas sensor having such a metal terminal can simultaneously achieve sufficient heat resistance of a forward end portion of the metal terminal, maintenance of electrical connection between the metal terminal and the sensor element (electrode terminal portion), and maintenance of electrical connection between the metal terminal and a lead wire.

Notably, the "material superior in heat resistance" means a material which has high creep resistance at high temperature and is unlikely to be susceptible to stress relaxation at high temperature. "0.2% Yield strength" is obtained in accordance with JIS 22241. "Elastic deformation" means deformation which is restored to an initial shape (original shape) before application of external force as a result of elimination of the external force.

In the above-mentioned gas sensor, the female connection portion and the male connection portion have contacting parts, which come into contact with each other and have a sectional shape of a circle or a regular polygon taken in a direction perpendicular to a direction of insertion.

In the metal terminal having such a structure, in connecting the forward terminal member and the rear terminal member, the relative position between the female connection portion and the male connection portion is adjusted according to the sectional shapes of the female and male connection portions; therefore, the forward terminal member and the rear terminal member can be readily connected without need to strictly adjust the relative position therebetween (in other words, the relative position between the female connection portion and the male connection portion).

For example, in the case where the sectional shape is a circle, even though the relative position between the female connection portion and the male connection portion in the direction of rotation about the direction of connection (direction of insertion) changes, since the sectional shapes are circles, the portions which come into contact with each other can maintain their shapes suited for connection. Thus, since the forward terminal member and the rear terminal member can be readily connected without need to strictly adjust the relative position therebetween, complication of connecting work can be mitigated.

In the case where the sectional shape is a regular polygon, even though the relative position between the female connection portion and the male connection portion in the direction of rotation about the direction of connection (direction of insertion) is unfitted for insertion, since the relative position in the direction of rotation is adjusted through mutual movement along a contact profile in the course of connecting work, complication of connecting work can be mitigated.

Notably, the concept "circle" with respect to the sectional shapes of the portions of the female connection portion and the male connection portion which come into contact with each other encompasses not only a breakless complete circle but also a circle having a break(s). Similarly, the concept "regular polygon" encompasses not only a breakless complete regular polygon but also a regular polygon having a break(s).

In the above-mentioned gas sensor, the rear terminal member may be formed such that a forward end portion of the male connection portion reduces in diameter in the forward direction.

In connecting the rear terminal member having such a structure to the forward terminal member, if at least the forward apex of the male connection portion is in a condition insertable into the female connection portion, even though the center axis of the female connection portion and the center axis of the male connection portion are misaligned from each other, the rear terminal member can be connected to the forward terminal member through movement of a forward end portion of the male connection portion along the inner wall surface of the female connection portion.

Thus, in the gas sensor having such a rear terminal member, the work of connecting the forward terminal member and the rear terminal member is facilitated.

In the above-mentioned gas sensor, the forward terminal member may be formed such that a rear end portion of the female connection portion increases in diameter in the rearward direction.

In connecting the forward terminal member having such a structure to the rear terminal member, if at least the forward apex of the male connection portion is in a condition insertable into a rear end portion of the female connection portion, even though the center axis of the female connection portion and the center axis of the male connection portion are misaligned from each other, the forward terminal member can be connected to the rear terminal member through movement of the male connection portion along the inner wall surface of the rear end portion of the female connection portion.

Thus, in the gas sensor having such a forward terminal member, the work of connecting the forward terminal member and the rear terminal member is facilitated.

Effect of the Invention

The gas sensor of the present invention can simultaneously achieve sufficient heat resistance of a forward end portion of a metal terminal, maintenance of electrical connection between the metal terminal and a sensor element (electrode terminal portion), and maintenance of electrical connection between the metal terminal and a lead wire.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Embodiments of the present invention will next be described with reference to the drawings.

The present invention is not limited to the following embodiments, but can be embodied in various modes without departing from the technical scope of the present invention.

1. First Embodiment

[1-1. Overall Configuration]

A first embodiment will be described while referring to an oxygen sensor (hereinafter, may be called a gas sensor 1) which is attached to an exhaust pipe of an internal combustion engine with a forward end portion thereof protruding into the exhaust pipe, for detecting oxygen contained in exhaust gas. The gas sensor 1 is attached to an exhaust pipe of a vehicle such as an automobile or a motorcycle.

First, the configuration of the gas sensor 1 of the present embodiment will be described with reference to FIG. 1.

Figure 1:
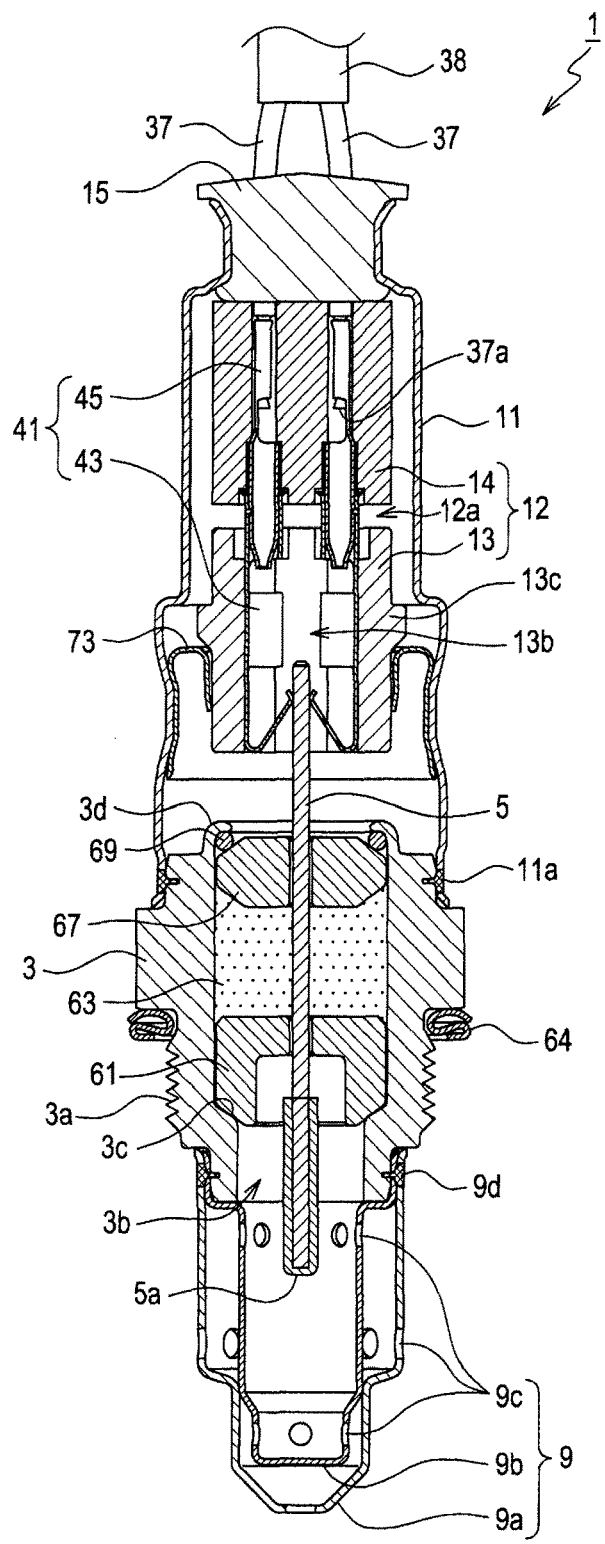
FIG. 1 is a sectional view showing the overall configuration of a gas sensor according to an embodiment of the present invention.

In FIG. 1, a lower side of the drawing corresponds to a forward side of the gas sensor, and an upper side corresponds to a rear side of the gas sensor.

The gas sensor 1 includes a tubular metallic shell 3 to be fixed to an exhaust pipe (not shown); a plate-like detection element 5 inserted through the metallic shell 3 and extending in the axial direction (the longitudinal direction of the gas sensor 1, or the vertical direction in FIG. 1); an element protector 9 disposed on the forward side (the lower side in FIG. 1) of the metallic shell 3 and covering a forward end portion of the detection element 5; a sleeve 11 attached to a rear end portion (an upper end portion in FIG. 1) of the metallic shell 3 through a weld zone 11a and radially surrounding the detection element 5; an insulating separator 12 disposed inside the sleeve 11 and accommodating a rear end portion of the detection element 5; a plug member 15 plugging a rear end portion of the sleeve 11; a plurality of (four in the present embodiment) metal terminals 41; and a plurality of (four in the present embodiment) lead wires 37.

The detection element 5 has a detecting section 19 formed at its forward end portion directed toward an object of measurement (exhaust gas, etc.,) and covered with a protection layer 5a, and electrode terminal portions (first to fourth electrode terminal portions) 31, 32, 34, and 35 formed on the outer surface of its rear end portion; i.e., on the front and back surfaces of the rear end portion; specifically, on a first plate surface 21 and a second plate surface 23 of the rear end portion.

The detection element 5 is fixed inside the metallic shell 3 such that the forward detecting section 19 protrudes from the forward end of the metallic shell 3 fixed to the exhaust pipe, whereas the rear electrode terminal portions 31, 32, 34, and 35 protrude from the rear end of the metallic shell 3.

The metal terminals 41 are connected to the electrode terminal portions 31, 32, 34, and 35, respectively. Specifically, a plurality of the metal terminals 41 are disposed inside the insulating separator 12 between the detection element 5 and the insulating separator 12, thereby being electrically connected to the electrode terminal portions 31, 32, 34, and 35, respectively, of the detection element 5. Each of the metal terminals 41 is composed of a forward terminal member 43 and a rear terminal member 45.

A plurality of the metal terminals 41 are electrically connected to a plurality of the lead wires 37 (specifically cores 37a of the lead wires 37), respectively, which are disposed inside the gas sensor 1 from the outside.

The structure of the metal terminal 41 will be described later in detail.

The metal terminals 41 and the lead wires 37 form current paths through which electric current flows between the detection element 5 (specifically, the electrode terminal portions 31, 32, 34, and 35) and external equipment (not shown) connected to the lead wires 37. A plurality of the lead wires 37 are bundled in a tube member 38. FIG. 1 shows only two of the lead wires 37.

Figure 2:
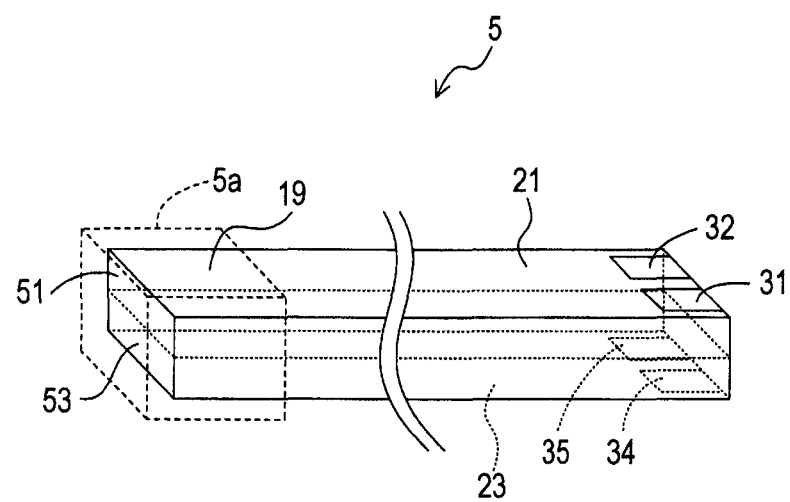
FIG. 2 is a perspective view showing the schematic structure of a detection element.

FIG. 2 is a perspective view showing a schematic structure of the detection element 5. FIG. 2 shows the detection element 5 with its axially intermediate portion eliminated.

As shown in FIG. 2, the detection element 5 is a rectangular parallelepiped laminate of a plate-like element body 51 extending in the axial direction (the horizontal direction in FIG. 2) and a plate-like heater 53 extending in the axial direction and has a rectangular section taken perpendicularly to the axial direction. In FIG. 2, the protection layer 5a is indicated by the dotted line.

Since the detection element 5 of the gas sensor 1 is a publicly known element, a detailed description of its internal structure, etc., is omitted, but its schematic structure is as follows.

First, the element body 51 includes, for example, an oxygen concentration cell formed by forming porous electrodes on respective opposite sides of a solid electrolyte substrate, and a spacer for forming a hollow reference gas chamber. The solid electrolyte substrate is formed of, for example, zirconia which contains yttria as a stabilizer in solid solution, and the porous electrodes are formed primarily of Pt, for example. The spacer used to form the reference gas chamber is formed primarily of alumina, and one of the two porous electrodes of the oxygen concentration cell is exposed to the interior of the hollow reference gas chamber. The spacer is formed such that the reference gas chamber is located at least at a forward end portion of the element body 51, and has a gas passage for introducing reference gas (air, for example) from outside into the reference gas chamber. A region of the element body 51 where the porous electrodes and the reference gas chamber are formed corresponds to the detecting section 19.

Meanwhile, the heater 53 is formed such that a heat generation resistor pattern formed primarily of Pt is sandwiched between insulating substrates formed primarily of alumina. The element body 51 and the heater 53 are joined together through a ceramic layer (zirconia ceramic or alumina ceramic, for example).

The detection element 5 has the protection layer 5a (not shown in FIG. 2) formed of porous ceramic on its forward end portion; at least, on the surface of the electrode to be exposed to an object of measurement (exhaust gas in the present embodiment), for the purpose of prevention of poisoning. As shown in FIG. 1, in the detection element 5 of the present embodiment, the protection layer 5a covers the entire surface of a forward end portion thereof which includes the surface of the porous electrode to be exposed to exhaust gas.

In the detection element 5 having such a structure, as shown in FIG. 2, two electrode terminal portions 31 and 32 are formed on a rear end portion (a right end portion in FIG. 2) of the first plate surface 21, and two electrode terminal portions 34 and 35 are formed on a rear end portion of the second plate surface 23. The electrode terminal portions 31 and 32 are formed on the element body 51 and are electrically connected to a pair of the porous electrodes, respectively, of the oxygen concentration cell. The electrode terminal portions 34 and 35 are formed on the heater 53 and are connected to opposite ends, respectively, of the heat generation resistor pattern through via conductors (not shown) extending through the heater in the heater thickness direction.

Referring back to FIG. 1, the metallic shell 3 is a tubular member having a threaded portion 3a formed on its outer surface for fixing the same to the exhaust pipe, and having a central through hole 3b extending therethrough in the axial direction. The metallic shell 3 has a ledge portion 3c protruding radially inward from the wall of the through hole 3b. The metallic shell 3 is formed of a metal material (e.g., stainless steel).

The through hole 3b of the metallic shell 3 accommodates an annular holder 61 (an annular ceramic holder 61) formed of an insulating material (e.g., alumina) and disposed in such a manner as to radially surround the detection element 5, an annular charged powder layer 63 (a talc ring 63), and an annular sleeve 67 (an annular ceramic sleeve 67) formed of an insulating material (e.g., alumina), which are stacked in this order from the forward side.

A crimp packing 69 is disposed between the ceramic sleeve 67 and a rear end portion 3d of the metallic shell 3. The rear end portion 3d of the metallic shell 3 is crimped so as to press forward the ceramic sleeve 67 through the crimp packing 69.

An annular gasket 64 is disposed rearward of the threaded portion 3a around the outer circumference of the metallic shell 3. The gasket 64 restrains leakage of gas from between the gas sensor 1 and a sensor attachment region (exhaust pipe).

The element protector 9 is a tubular member attached to the outer circumference of a forward end portion of the metallic shell 3 through a weld zone 9d in such a manner as to cover a protruding portion of the detection element 5. The element protector 9 is formed of a heat resistant material (e.g., SUS310S). The element protector 9 has a dual structure consisting of an outer protector 9a and an inner protector 9b. The outer protector 9a and the inner protector 9b have a plurality of holes 9c formed in the side wall or in a forward end portion for allowing passage of gas therethrough.

The insulating separator 12 can be divided into a forward separator 13 and a rear separator 14.

The forward separator 13 is a tubular member formed of an insulating material (e.g., alumina) and is held to the inner wall of the sleeve 11 by a tubular metal holding member 73 disposed within the sleeve 11. The forward separator 13 has a terminal disposition hole 13b extending therethrough in the axial direction. The terminal disposition hole 13b accommodates a rear end portion (electrode terminal portions 31, 32, 34, and 35) of the detection element 5, and forward portions (specifically, the forward terminal members 43) of a plurality of the metal terminals 41 to be electrically connected to the electrode terminal portions 31, 32, 34, and 35, respectively. The forward separator 13 has an annular collar portion 13c protruding outward from the outer surface thereof. The axial position of the forward separator 13 can be fixed within the sleeve 11 by means of the collar portion 13c coming into contact with the metal holding member 73.

The rear separator 14 is a tubular member formed of an insulating material (e.g., alumina) and is disposed forward of the plug member 15 within the sleeve 11. The rear separator 14 has a plurality of terminal disposition holes 14b extending therethrough in the axial direction. The rear separator 14 accommodates rear portions (specifically, the rear terminal members 45) of the metal terminals 41 in a plurality of the terminal disposition holes 14b, respectively.

The structure of the insulating separator 12 (the forward separator 13 and the rear separator 14) will be described in detail later.

The plug member 15 is a grommet formed of a flexible material (e.g., fluororesin). The plug member 15 is disposed in a rear-end opening portion of the sleeve 11 and is fixed to the sleeve 11 by means of the sleeve 11 being crimped inward from outside. The plug member 15 has a plurality of through holes (not shown) formed therein for allowing a plurality of the lead wires 37 to be inserted through the through holes, respectively.

A plurality of the lead wires 37 are connected (by crimping) to rear end portions of the metal terminals 41, respectively, are inserted respectively through the through holes extending through the plug member 15, and extend outward.

[1-2. Metal Terminal]

Next, the metal terminal 41 will be described.

As mentioned above, the metal terminal 41 is composed of the forward terminal member 43 and the rear terminal member 45. That is, the metal terminal 41 is not a single member, but is composed of the forward terminal member 43 and the rear terminal member 45.

Figure 3:
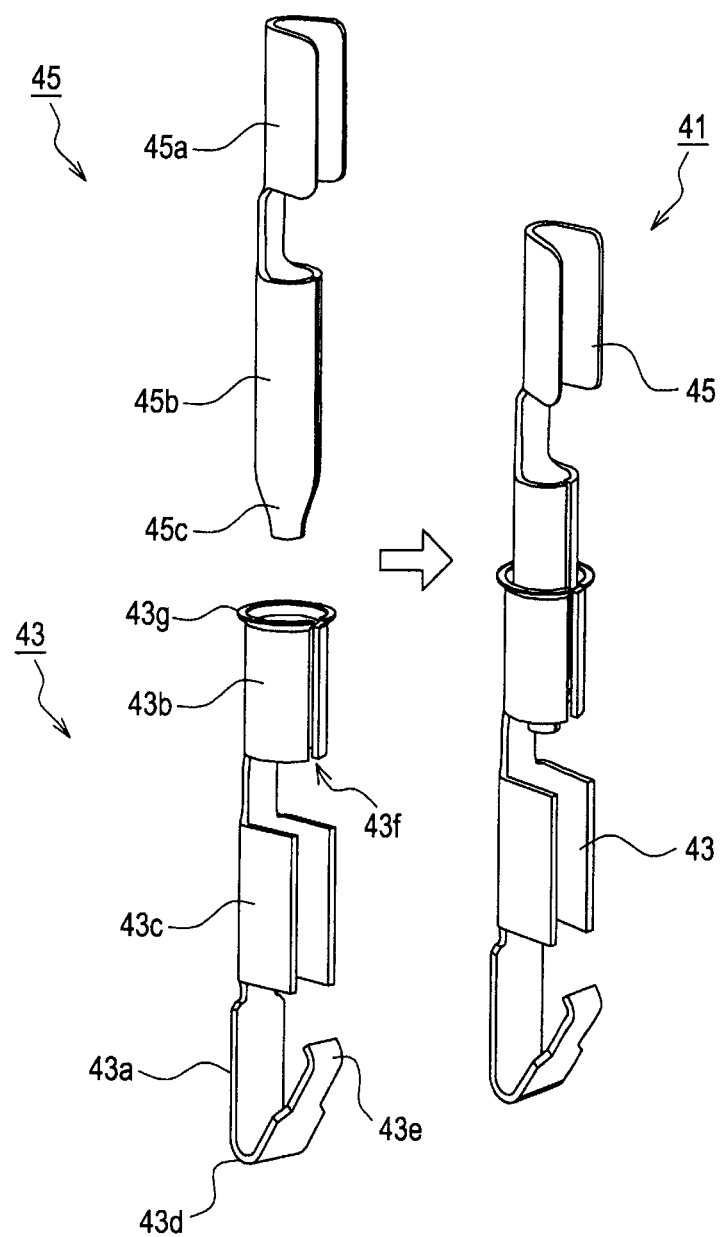
FIG. 3 is an explanatory view showing the structure of a metal terminal composed of a forward terminal member and a rear terminal member.

FIG. 3 is an explanatory view showing the structure of the metal terminal 41 composed of the forward terminal member 43 and the rear terminal member 45.

The forward terminal member 43 is formed of a metal material which can maintain elasticity (spring elasticity) even in repeated exposure to high temperature; for example, an alloy material which predominantly contains Ni (NCF718 or the like). The forward terminal member 43 is formed by bending an elongated sheet-like metal material and includes a body portion 43a, a female connection portion 43b, extension portions 43c, a bend portion 43d, and an element contact portion 43e.

The body portion 43a has an elongated plate-like shape extending in the axial direction.

The female connection portion 43b is located rearward of the body portion 43a, has a tubular shape, and has a circular section taken perpendicularly to the axial direction. The female connection portion 43b has a slit 43f for allowing a change of the inside diameter of the tubular shape in response to elastic deformation. Thus, the sectional shape of the female connection portion 43b is strictly a circle with a break. The female connection portion 43b also has a rear-end diameter-expanding portion 43g. The diameter-expanding portion 43g is shaped such that the diameter increases rearward.

The extension portions 43c extend from the sides of the body portion 43a in a direction perpendicular to the plate surface of the body portion 43a. Two extension portions 43c extend from the body portion 43a. The extension portions 43c improve the strength of the body portion 43a.

The bend portion 43d is bent in a direction perpendicular to the plate surface of the body portion 43a at the forward end of the body portion 43a and connects the body portion 43a and the element contact portion 43e.

The element contact portion 43e is connected to the body portion 43a through the bend portion 43d, and the size of the gap between the body portion 43a and the element contact portion 43e can be changed through elastic deformation of the bend portion 43d.

The forward terminal member 43 having such a structure can maintain contact between the element contact portion 43e and the detection element 5 through elastic deformation of the bend portion 43d resulting from contact of the element contact portion 43e with the detection element 5 (specifically, the electrode terminal portion 31, 32, 34, or 35).

Next, the rear terminal member 45 is formed of a metal material, such as a stainless steel alloy (SUS304), smaller in "0.2% yield strength" than a metal material used to form the forward terminal member 43. The rear terminal member 45 is formed by bending an elongated sheet-like metal material and includes a signal-wire connection portion 45a and a male connection portion 45b.

The signal-wire connection portion 45a is deformed, by bending, into such a tubular shape as to surround the core 37a of the lead wire 37 (see FIG. 1). The signal-wire connection portion 45a is crimped radially inward while surrounding the core 37a of the lead wire 37, thereby being mechanically and electrically connected to the core 37a of the lead wire 37.

The male connection portion 45b is located forward of the signal-wire connection portion 45a, has a tubular shape, and has a circular section taken perpendicularly to the axial direction. The male connection portion 45b has such an outside diameter as to allow insertion thereof into the female connection portion 43b. The male connection portion 45b has a forward-end diameter-reducing portion 45c. The diameter-reducing portion 45c is shaped such that the diameter reduces forward.

The rear terminal member 45 having such a structure is electrically connected to external equipment through the lead wire 37 as a result of the signal-wire connection portion 45a being electrically connected to the core 37a of the lead wire 37.

As shown at the right of FIG. 3, the metal terminal 41 is configured such that the forward terminal member 43 and the rear terminal member 45 are connected together. More specifically, the metal terminal 41 composed of the forward terminal member 43 and the rear terminal member 45 is formed through connection of the male connection portion 45b and the female connection portion 43b.

The metal terminal 41 having such a structure is configured such that the element contact portion 43e of the forward terminal member 43 is electrically connected to the detection element 5 (specifically, the electrode terminal portion 31, 32, 34, or 35) while the signal-wire connection portion 45a of the rear terminal member 45 is electrically connected to external equipment through the lead wire 37.

The forward terminal member 43 is formed of an alloy material which predominantly contains Ni, and the rear terminal member 45 is formed of a stainless steel alloy. An alloy material which predominantly contains Ni is superior in heat resistance to and greater in "0.2% yield strength" than a stainless steel alloy. That is, the forward terminal member 43 is formed of a material superior in heat resistance to and larger in elastic deformation region than a material used to form the rear terminal member 45.

[1-3. Insulating Separator]

Next, the insulating separator 12 will be described.

As mentioned above, the insulating separator 12 can be divided into the forward separator 13 and the rear separator 14.

Figure 4:
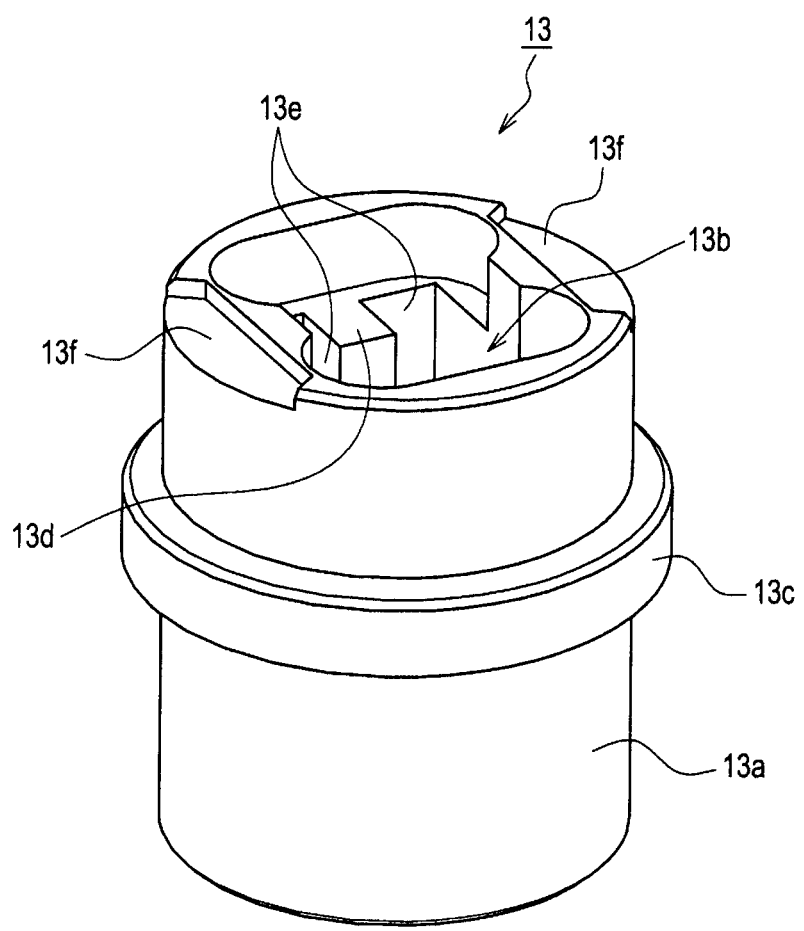
FIG. 4 is a perspective view of a forward separator as viewed from obliquely above on the rear side.
Figure 5:
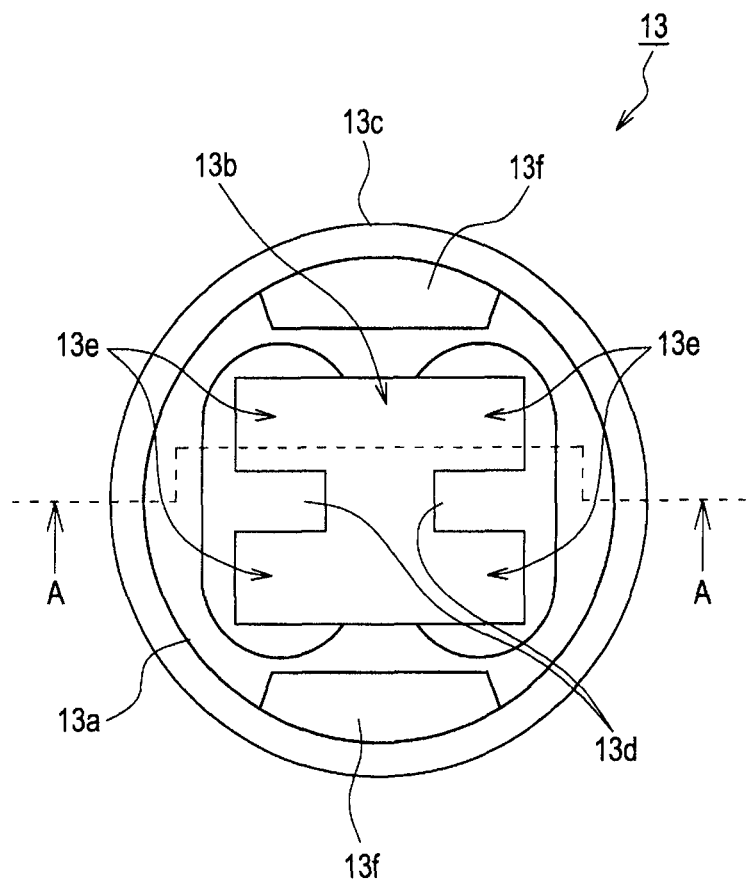
FIG. 5 is an exterior view of the forward separator as viewed from the rear side.
Figure 6:
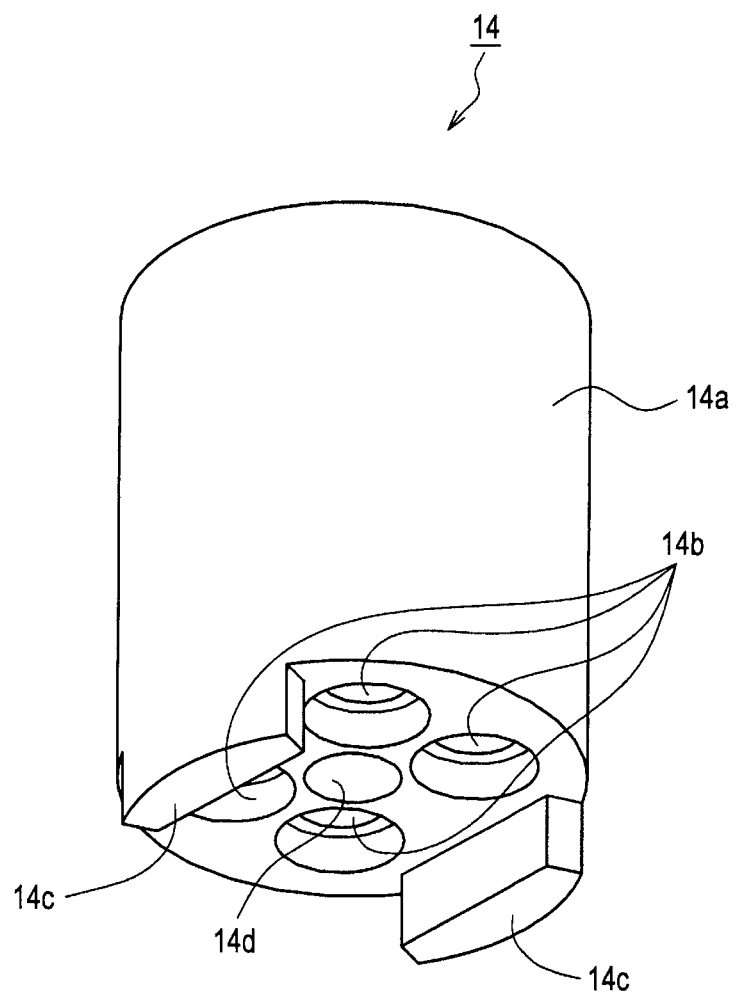
FIG. 6 is a perspective view of a rear separator as viewed from obliquely underneath on the forward side.
Figure 7:
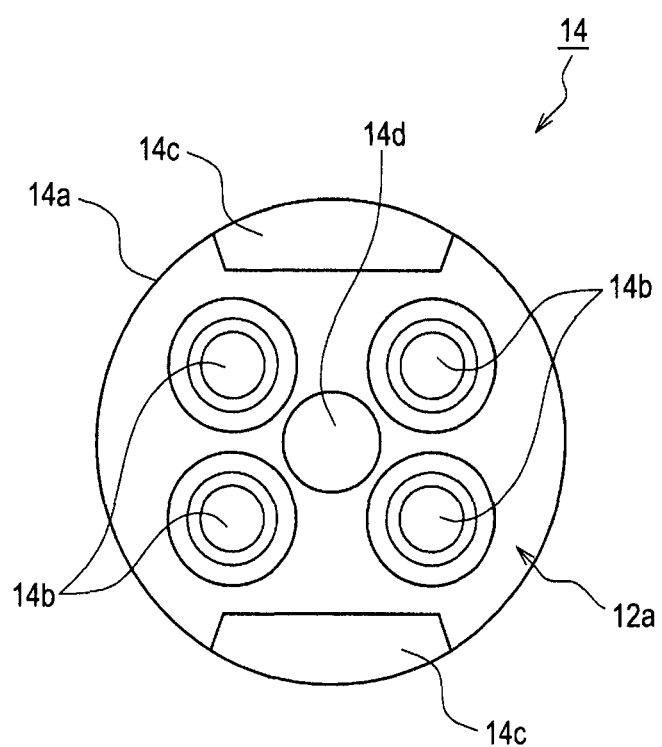
FIG. 7 is an exterior view of the rear separator as viewed from the forward side.

FIG. 4 is a perspective view of the forward separator 13 as viewed from obliquely above on the rear side, and FIG. 5 is an exterior view of the forward separator 13 as viewed from the rear side. FIG. 6 is a perspective view of the rear separator 14 as viewed from obliquely underneath on the forward side, and FIG. 7 is an exterior view of the rear separator 14 as viewed from the forward side. In the sectional view of the gas sensor 1 in FIG. 1, the section of the insulating separator 12 is taken along line A-A of FIG. 5.

First, the forward separator 13 will be described.

As mentioned above, the forward separator 13 is a tubular member formed of an insulating material (e.g., alumina). As shown in FIGS. 4 and 5, the forward separator 13 includes a tubular separator body portion 13a and a collar portion 13c.

The separator body portion 13a has a terminal disposition hole 13b extending therethrough in the axial direction. The separator body portion 13a has two partitions 13d protruding inward from the wall surface of the terminal disposition hole 13b and extending in the axial direction. Each partition 13d is formed between two terminal disposition regions 13e and prevents contact (electrical short circuit) between two metal terminals 41 (more specifically, two forward terminal members 43) disposed in the two adjacent terminal disposition regions 13e, respectively. The two partitions 13d are formed on the wall surface of the terminal disposition hole 13b in such a manner as to face each other.

That is, the forward separator 13 has four terminal disposition regions 13e in the terminal disposition hole 13b for allowing four metal terminals 41 (four forward terminal members 43) to be disposed therein in a mutually electrically insulated condition.

The terminal disposition hole 13b has such a size as to accommodate a rear end portion of the detection element 5 in a region between the two partitions 13d while the metal terminals 41 (the forward terminal members 43) are disposed in the four terminal disposition regions 13e, respectively.

That is, the forward separator 13 accommodates the four metal terminals 41 (the four forward terminal members 43) and a rear end portion of the detection element 5 in the terminal disposition hole 13b and establishes electrical connection between the four metal terminals 41 (the four forward terminal members 43) and the electrode terminal portions 31, 32, 34, and 35, respectively, of the detection element 5.

The collar portion 13c protrudes outward from the outer surface of the separator body portion 13a and is formed annularly along the outer surface of the separator body 13a.

The forward separator 13 also has two recesses 13f formed at the rear end of the separator body portion 13a.

Next, the rear separator 14 will be described.

As mentioned above, the rear separator 14 is a tubular member formed of an insulating material (e.g., alumina). As shown in FIGS. 6 and 7, the rear separator 14 includes a tubular separator body portion 14a and protrusions 14c.

The separator body portion 14a has a plurality of (four in the present embodiment) the terminal disposition holes 14b extending therethrough in the axial direction. Each of the terminal disposition holes 14b has a circular section taken perpendicularly to the axial direction and has such a size as to accommodate a rear end portion (the rear terminal member 45) of the metal terminal 41. In the rear separator 14, a single metal terminal 41 is disposed in a single terminal disposition hole 14b, thereby preventing contact (electrical short circuit) between the metal terminals 41 (more specifically, the rear terminal members 45).

The separator body portion 14a also has a ventilation hole 14d extending therethrough in the axial direction. By virtue of the rear separator 14 having the ventilation hole 14d, moisture or the like existing between the forward separator 13 and the rear separator 14 can be discharged outward through the ventilation hole 14d. The plug member 15 has a ventilation hole (not shown in FIG. 1) communicating with the ventilation hole 14d and with the outside.

The protrusions 14c protrude forward from the forward end of the separator body portion 14a. The two protrusions 14c are formed at the forward end of the separator body 14a. The positions of the protrusions 14c protruding from the separator body portion 14a correspond to the positions of the two recesses 13f of the forward separator 13 (separator body portion 13a).

Figure 8:
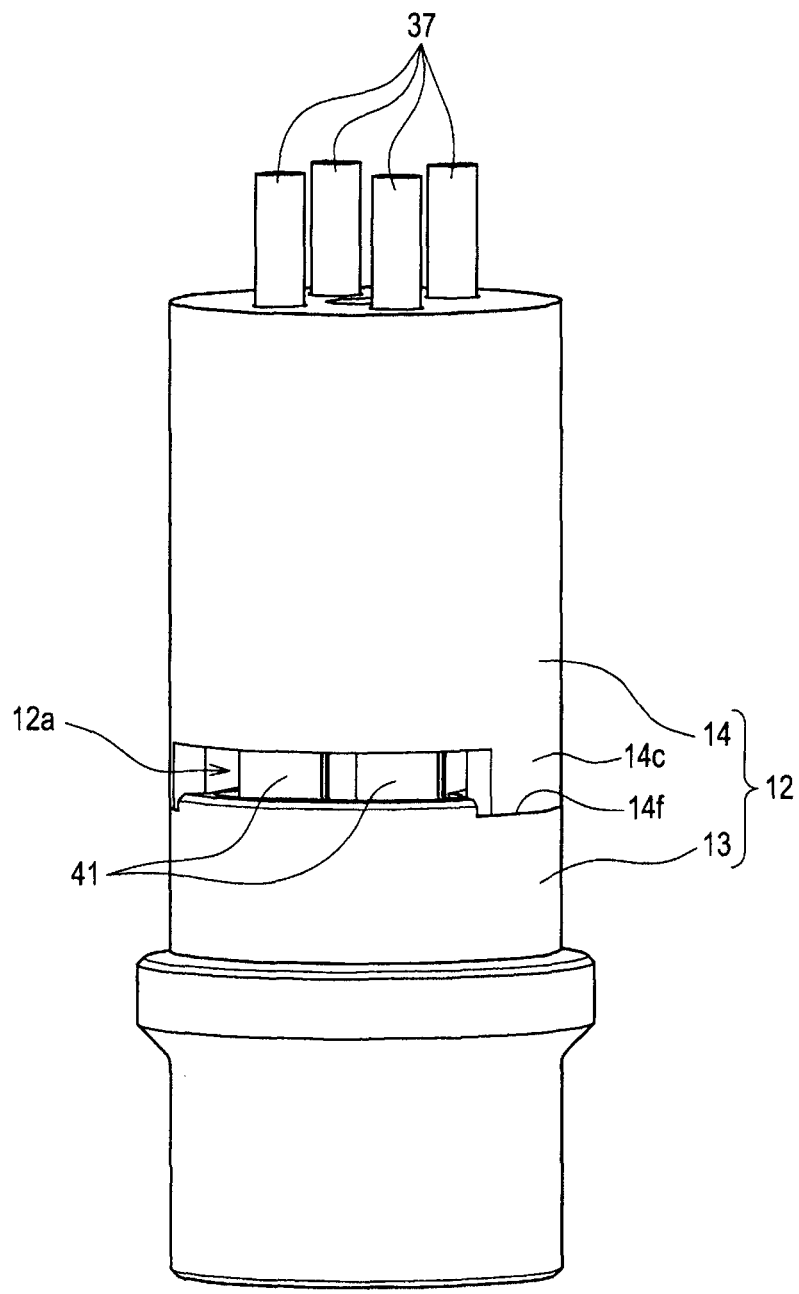
FIG. 8 is an explanatory exterior view showing an insulating separator with metal terminals disposed inside and the forward separator and the rear separator assembled together.

FIG. 8 is an explanatory exterior view showing an insulating separator 12 with the metal terminals 41 disposed inside and the forward separator 13 and the rear separator 14 assembled together.

The forward separator 13 and the rear separator 14 are assembled in such a manner that the two protrusions 14c of the rear separator 14 are engaged with the two recesses 13f, respectively, of the forward separator 13, thereby forming the insulating separator 12.

The insulating separator 12 is assembled, for example, as follows. First, a rear end portion of the detection element 5 and the four forward terminal members 43 are disposed in the terminal disposition hole 13b of the forward separator 13. Meanwhile, the lead wires 37 are inserted through the four terminal disposition holes 14b, respectively, of the rear separator 14; then, the cores 37a of the lead wires 37 are connected (fixed) to the signal-wire connection portions 45a of the rear terminal members 45, respectively, by crimping. Subsequently, the four forward terminal members 43 disposed in the terminal disposition hole 13b of the forward separator 13 and the four rear terminal members 45 are connected respectively; then, the rear separator 14 is moved toward the rear terminal members 45 along the lead wires 37, thereby accommodating (disposing) the four rear terminal members 45 in the terminal disposition holes 14b, respectively. At this time, the two protrusions 14c of the rear separator 14 are engaged with the two recesses 13f of the forward separator 13, respectively.

By this procedure, the forward separator 13 and the rear separator 14 are assembled together, thereby completing the insulating separator 12.

The insulating separator 12 has a ventilation path 12a in the form of a space defined by the protrusions 14c between the forward separator 13 and the rear separator 14. The ventilation path 12a includes a side space extending from the side surface of the insulating separator 12 to the metal terminals 41 and an inner space communicating with all the metal terminals 41.

[1-4. Effect]

As described above, in the gas sensor 1 of the present embodiment, the metal terminal 41 is composed of the forward terminal member 43 and the rear terminal member 45.

The forward terminal members 43 and the rear terminal members 45 electrically connect the electrode terminal portions 31, 32, 34, and 35 of the detection element 5 and the lead wires 37 (the cores 37a), respectively, in such a condition that the female connection portions 43b and the male connection portions 45b are connected, respectively.

The forward terminal member 43 is formed of an alloy material which predominantly contains Ni, and the rear terminal member 45 is formed of a stainless steel alloy. That is, the forward terminal member 43 is formed of a material superior in heat resistance to and greater in "0.2% yield strength" than a material used to form the rear terminal member 45.

Since the metal terminal 41 is composed of the forward terminal member 43 and the rear terminal member 45 formed of materials having different characteristics, respectively, a portion of the metal terminal 41 in contact with the detection element 5 and a portion of the metal terminal 41 connected to the lead wire 37 differ in characteristics.

Since the forward terminal member 43 is formed of a material superior in heat resistance to and greater in "0.2% yield strength" than a material used to form the rear terminal member 45, the forward terminal member 43 has heat resistance suitable for a portion which comes into contact with the high-temperature detection element 5 and is large in elastic deformation region, thereby providing good contact with the detection element 5 (specifically, the electrode terminal portion 31, 32, 34, or 35) and facilitating maintenance of electrical contact with the detection element 5.

Since the rear terminal member 45 is formed of a material having "0.2% yield strength" equivalent to or smaller than that of a material used to form the forward terminal member 43, in connecting (fixing) the signal-wire connection portion 45a to the lead wire 37 by crimping, springback is unlikely to occur at the signal-wire connection portion 45a. Since such a rear terminal member 45 provides firm connection between the signal-wire connection portion 45a and the lead wire 37, the rear terminal member 45 facilitates maintenance of electrical connection with the lead wire 37.

Thus, the gas sensor 1 having such metal terminals 41 can simultaneously achieve sufficient heat resistance of forward end portions of the metal terminals 41, maintenance of electrical connection between the metal terminals 41 and the detection element 5 (specifically, the electrode terminal members 31, 32, 34, and 35), and maintenance of electrical connection between the metal terminals 41 and the lead wires 37, respectively.

Next, in the gas sensor 1, the portions of the female connection portion 43b and the male connection portion 45b which come into contact with each other have a sectional shape of a circle taken in a direction perpendicular to a direction of insertion.

In the metal terminal 41 having such a structure, in connecting the forward terminal member 43 and the rear terminal member 45, the relative position between the female connection portion 43b and the male connection portion 45b is adjusted according to the sectional shapes of the female connection portion 43b and the male connection portion 45b; therefore, the forward terminal member 43 and the rear terminal member 45 can be readily connected without need to strictly adjust the relative position therebetween (in other words, the relative position between the female connection portion 43b and the male connection portion 45b).

That is, in the case of a sectional shape of a circle, even though the relative position between the female connection portion 43b and the male connection portion 45b in a direction of rotation about a direction of connection (direction of insertion) changes, since the sectional shapes are circles, mutual contact can maintain a condition suited for connecting work. Thus, since the forward terminal member 43 and the rear terminal member 45 can be readily connected without need to strictly adjust the relative position therebetween, complication of connecting work can be mitigated.

Next, in the gas sensor 1, the rear terminal member 45 is formed such that a forward end portion of the male connection portion 45b assumes the form of the diameter-reducing portion 45c whose diameter reduces forward.

In connecting the rear terminal member 45 having such a structure to the forward terminal member 43, if at least the forward apex of the male connection portion 45b is in a condition insertable into the female connection portion 43b, even though the center axis of the female connection portion 43b and the center axis of the male connection portion 45b are misaligned from each other, the rear terminal member 45 can be connected to the forward terminal member 43 through movement of a forward end portion (the diameter-reducing portion 45c) of the male connection portion 45b along the inner wall surface of the female connection portion 43b.

Thus, in the gas sensor 1 having such rear terminal members 45, the work of connecting the forward terminal members 43 and the rear terminal members 45, respectively, is facilitated.

Next, in the gas sensor 1, the forward terminal member 43 is formed such that a rear end portion of the female connection portion 43b assumes the form of the diameter-expanding portion 43g whose diameter increases rearward.

In connecting the forward terminal member 43 having such a structure to the rear terminal member 45, if at least the forward apex of the male connection portion 45b is in a condition insertable into a rear end portion (the diameter-expanding portion 43g) of the female connection portion 43b, the forward terminal member 43 can be connected to the rear terminal member 45. That is, even though the center axis of the female connection portion 43b and the center axis of the male connection portion 45b are misaligned from each other, the forward terminal member 43 and the rear terminal member 45 can be connected through movement of the male connection portion 45b along the inner wall surface of the rear end portion (the diameter-expanding portion 43g) of the female connection portion 43b.

Thus, in the gas sensor 1 having such forward terminal members 43, the work of connecting the forward terminal members 43 and the rear terminal members 45, respectively, is facilitated.

[1-5. Terminological Correspondence]

The terminological correspondence between the present embodiment and claims will be described.

The gas sensor 1 corresponds to an example of the gas sensor; the detection element 5 corresponds to an example of the sensor element; the metal terminal 41 corresponds to an example of the metal terminal; and the lead wire 37 corresponds to an example of the signal wire.

The forward terminal member 43 corresponds to an example of the forward terminal member; the rear terminal member 45 corresponds to an example of the rear terminal member; the female connection portion 43b corresponds to an example of the female connection portion; and the male connection portion 45b corresponds to an example of the male connection portion.

2. Second Embodiment

[2-1. Overall Configuration]

A second embodiment will be described while referring to a gas sensor having second metal terminals 141 and a second insulating separator 112.

The second metal terminal 141 differs from the metal terminal 41 of the first embodiment in the sectional shapes of a female connection portion and a male connection portion.

Since the second embodiment differs from the first embodiment in the structures of the metal terminal and the insulating separator, the second embodiment will be described, centering on the metal terminal and the insulating separator. In the following description of the second embodiment, structural features similar to those of the first embodiment will be described by use of reference numerals similar to those of the first embodiment, or description thereof will be omitted.

[2-2. Second Metal Terminal]

First, the second metal terminal 141 will be described.

Figure 9:
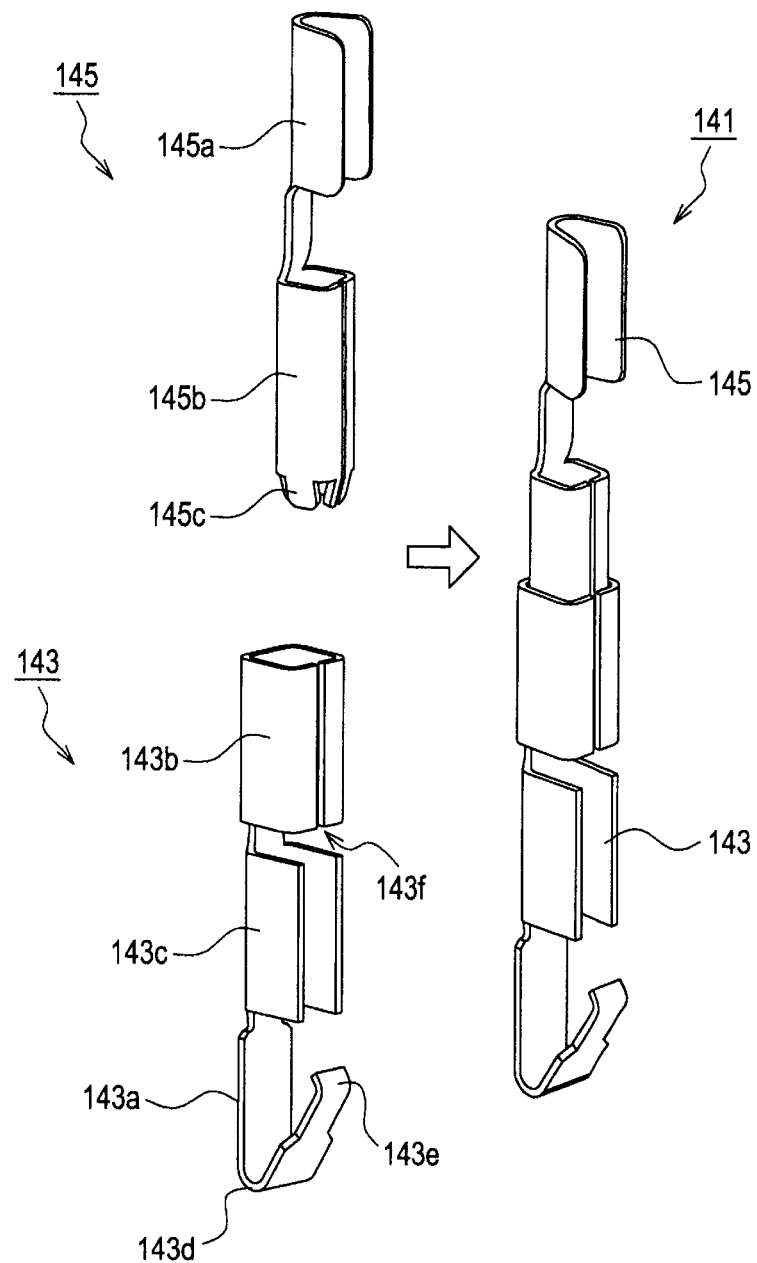
FIG. 9 is an explanatory view showing the structure of a second metal terminal composed of a second forward terminal member and a second rear terminal member.

FIG. 9 is an explanatory view showing the structure of the second metal terminal 141.

The second metal terminal 141 is composed of a second forward terminal member 143 and a second rear terminal member 145. That is, the second metal terminal 141 is not a single member, but can be divided into the second forward terminal member 143 and the second rear terminal member 145.

The second forward terminal member 143 is formed of a metal material which can maintain elasticity (spring elasticity) even in repeated exposure to high temperature; for example, an alloy material which predominantly contains Ni (NCF718 or the like). The second forward terminal member 143 is formed by bending an elongated sheet-like metal material and includes a body portion 143a, a female connection portion 143b, extension portions 143c, a bend portion 143d, and an element contact portion 143e.

Since the body portion 143a, the extension portions 143c, the bend portion 143d, and the element contact portion 143e of the second forward terminal member 143 are similar in structure to the body portion 43a, the extension portions 43c, the bend portion 43d, and the element contact portion 43e, respectively, of the forward terminal member 43 of the first embodiment, description thereof is omitted.

The female connection portion 143b is located rearward of the body portion 143a, has a tubular shape, and has a regular polygonal section (specifically, a square section) taken perpendicularly to the axial direction. The female connection portion 143b has a slit 143f for allowing a change of the inside diameter of the tubular shape in response to elastic deformation. Thus, the sectional shape of the female connection portion 143b is strictly a regular polygon with a break.

The second forward terminal member 143 having such a structure can maintain contact between the element contact portion 143e and the detection element 5 through elastic deformation of the bend portion 143d resulting from contact of the element contact portion 143e with the detection element 5 (specifically, the electrode terminal portion 31, 32, 34, or 35).

Next, the second rear terminal member 145 is formed of a metal material, such as a stainless steel alloy (SUS304), less elastically deformable than a material used to form the second forward terminal member 143. The second rear terminal member 145 is formed by bending an elongated sheet-like metal material and includes a signal-wire connection portion 145a and a male connection portion 145b.

Since the signal-wire connection portion 145a of the second rear terminal member 145 is similar in structure to the signal-wire connection portion 45a of the rear terminal member 45 of the first embodiment, description thereof is omitted.

The male connection portion 145b is located forward of the signal-wire connection portion 145a, has a tubular shape, and has a regular polygonal section (specifically, a square section) taken perpendicularly to the axial direction. The male connection portion 145b has such an outside diameter as to allow insertion thereof into the female connection portion 143b. The male connection portion 145b has a forward-end diameter-reducing portion 145c. The diameter-reducing portion 145c is shaped such that the diameter reduces forward.

The second rear terminal member 145 having such a structure is electrically connected to external equipment through the lead wire 37 as a result of the signal-wire connection portion 145a being electrically connected to the core 37a of the lead wire 37.

As shown at the right of FIG. 9, the second metal terminal 141 is configured such that the second forward terminal member 143 and the second rear terminal member 145 are connected together. More specifically, the second metal terminal 141 composed of the second forward terminal member 143 and the second rear terminal member 145 is formed through connection of the male connection portion 145b and the female connection portion 143b.

The second metal terminal 141 having such a structure is configured such that the element contact portion 143e of the second forward terminal member 143 is electrically connected to the detection element 5 (specifically, the electrode terminal portion 31, 32, 34, or 35) while the signal-wire connection portion 145a of the second rear terminal member 145 is electrically connected to external equipment through the lead wire 37.

The second forward terminal member 143 is formed of an alloy material which predominantly contains Ni, and the second rear terminal member 145 is formed of a stainless steel alloy. An alloy material which predominantly contains Ni is superior in heat resistance to and greater in "0.2% yield strength" than a stainless steel alloy. That is, the second forward terminal member 143 is formed of a material superior in heat resistance to and larger in elastic deformation region than a material used to form the second rear terminal member 145.

[2-3. Second Insulating Separator]

Next, a second insulating separator 112 provided in a gas sensor of the second embodiment will be described.

The second insulating separator 112 can be divided into the forward separator 13 and a second rear separator 114.

That is, as compared with the insulating separator 12 of the first embodiment, the second insulating separator 112 is composed of the same forward separator 13 and the second rear separator 114 in place of the rear separator 14.

Since the second rear separator 114 is similar in exterior appearance to the rear separator 14, the exterior appearance of the second insulating separator 112 is similar to that of the insulating separator 12 of the first embodiment (see FIG. 8).

The second rear separator 114 is a tubular member formed of an insulating material (e.g., alumina).

Figure 10:
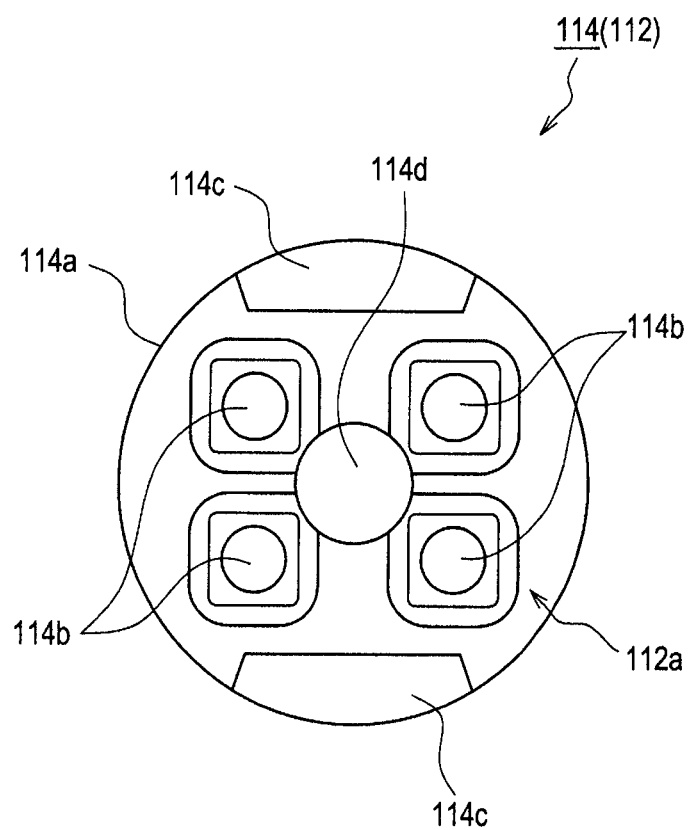
FIG. 10 is an exterior view of a second rear separator as viewed from the forward side.

FIG. 10 is an exterior view of the second rear separator 114 as viewed from the forward side.

As shown in FIG. 10, the second rear separator 114 includes a tubular separator body portion 114a and protrusions 114c.

The separator body portion 114a has a plurality of (four in the present embodiment) terminal disposition holes 114b extending therethrough in the axial direction. Each of the terminal disposition holes 114b has a regular polygonal section (specifically, a square section) taken perpendicularly to the axial direction and has such a size as to accommodate a rear end portion (the second rear terminal member 145) of the second metal terminal 141. In the second rear separator 114, a single second metal terminal 141 is disposed in a single terminal disposition hole 114b, thereby preventing contact (electrical short circuit) between the second metal terminals 141 (more specifically, the second rear terminal members 145).

The separator body portion 114a also has a ventilation hole 114d extending therethrough in the axial direction. By virtue of the second rear separator 114 having the ventilation hole 114d, moisture or the like existing between the forward separator 13 and the second rear separator 114 can be discharged outward through the ventilation hole 114d. The plug member 15 has a ventilation hole (not shown in FIG. 1) communicating with the ventilation hole 114d and with the outside.

The protrusions 114c protrude forward from the forward end of the separator body portion 114a. The two protrusions 114c are formed at the forward end of the separator body 114a.

That is, the second rear separator 114 is similar in exterior appearance to the rear separator 14, but the sectional shape of the terminal disposition holes 114b differs from that of the terminal disposition holes 14b. The second insulating separator 112 has a ventilation path 112a in the form of a space defined by the protrusions 114c between the forward separator 13 and the second rear separator 114.

[2-4. Effect]

As described above, in the gas sensor of the second embodiment, the second metal terminal 141 is composed of the second forward terminal member 143 and the second rear terminal member 145.

The second forward terminal member 143 is formed of the same material as that used to form the forward terminal member 43 of the first embodiment, and the second rear terminal member 145 is formed of the same material as that used to form the rear terminal member 45 of the first embodiment.

Since the second forward terminal member 143 is formed of a material superior in heat resistance to and greater in "0.2% yield strength" than a material used to form the second rear terminal member 145, the second forward terminal member 143 has heat resistance suitable for contact with the high-temperature detection element 5 and is larger in elastic deformation region than the second rear terminal member 145, thereby providing good contact with the detection element 5 (more specifically, the electrode terminal portion 31, 32, 34, or 35) and facilitating maintenance of electrical contact with the detection element 5.

Since the second rear terminal member 145 is formed of a material having "0.2% yield strength" equivalent to or smaller than that of a material used to form the second forward terminal member 143, in connecting (fixing) the signal-wire connection portion 145a to the lead wire 37 by crimping, springback is unlikely to occur at the signal-wire connection portion 145a. Since such a second rear terminal member 145 provides firm connection between the signal-wire connection portion 145a and the lead wire 37, the second rear terminal member 145 facilitates maintenance of electrical connection with the lead wire 37.

Thus, the gas sensor having such second metal terminals 141 can simultaneously achieve sufficient heat resistance of forward end portions of the second metal terminals 141, maintenance of electrical connection between the second metal terminals 141 and the detection element 5 (specifically, the electrode terminal members 31, 32, 34, and 35), and maintenance of electrical connection between the second metal terminals 141 and the lead wires 37, respectively.

Next, in the second metal terminal 141, the portions of the female connection portion 143b and the male connection portion 145b which come into contact with each other have a sectional shape of a regular polygon (specifically, a square) taken in a direction perpendicular to the direction of insertion.

In the second metal terminal 141 having such a structure, in connecting the second forward terminal member 143 and the second rear terminal member 145, the relative position between the female connection portion 143b and the male connection portion 145b is adjusted according to the sectional shapes of the female and male connection portions 143b and 145b; therefore, the second forward terminal member 143 and the second rear terminal member 145 can be readily connected without need to strictly adjust the relative position therebetween (in other words, the relative position between the female connection portion 143b and the male connection portion 145b).

That is, in the case of a sectional shape of a regular polygon, even though the relative position between the female connection portion 143b and the male connection portion 145b in the direction of rotation about the direction of connection (direction of insertion) is unfitted for insertion, since the relative position in the direction of rotation is adjusted through mutual movement along a contact profile in the course of connecting work, complication of connecting work can be mitigated.

Next, in the second metal terminal 141, the second rear terminal member 145 is formed such that a forward end portion of the male connection portion 145b assumes the form of the diameter-reducing portion 145c whose diameter reduces forward.

In connecting the second rear terminal member 145 having such a structure to the second forward terminal member 143, if at least the forward apex of the male connection portion 145b is in a condition insertable into the female connection portion 143b, even though the center axis of the female connection portion 143b and the center axis of the male connection portion 145b are misaligned from each other, the second rear terminal member 145 can be connected to the second forward terminal member 143 through movement of a forward end portion (the diameter-reducing portion 145c) of the male connection portion 145b along the inner wall surface of the female connection portion 143b.

Thus, in the second metal terminal member 141 having such a second rear terminal member 145, the work of connecting the second forward terminal member 143 and the second rear terminal member 145 is facilitated.

[2-5. Terminological Correspondence]

The terminological correspondence between the present embodiment and claims will be described.

The second metal terminal 141 corresponds to an example of the metal terminal; the second forward terminal member 143 corresponds to an example of the forward terminal member; the second rear terminal member 145 corresponds to an example of the rear terminal member; the female connection portion 143b corresponds to an example of the female connection portion; and the male connection portion 145b corresponds to an example of the male connection portion.

3. Other Embodiments

While the present invention has been described with reference to the above embodiments, the present invention is not limited thereto, but may be embodied in various other forms without departing from the gist of the invention.

Figure 11:
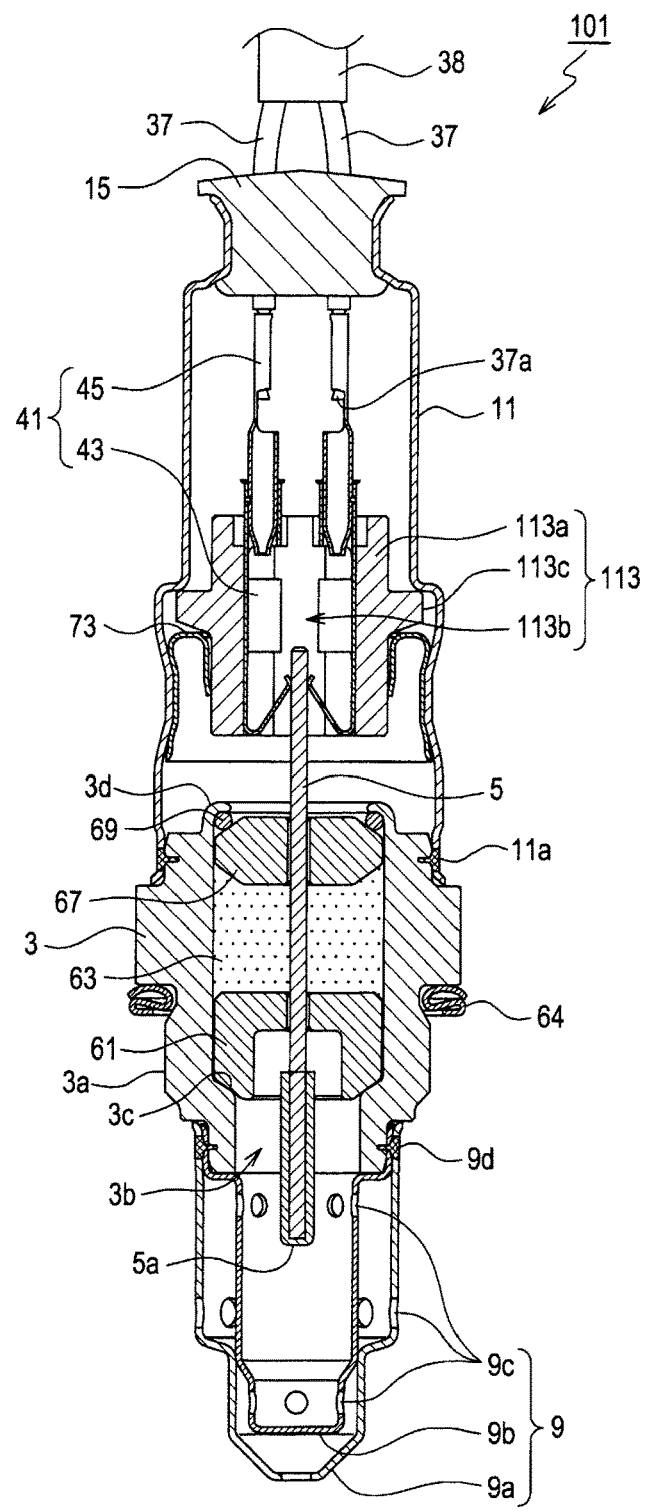
FIG. 11 is a sectional view showing the overall configuration of a second gas sensor.

For example, the above embodiments are described while referring to the insulating separator which can be divided into the forward separator and the rear separator. However, the insulating separator may assume the form of a single member. For example, as in the case of a second gas sensor 101 shown in FIG. 11, the insulating separator may assume the form of a third insulating separator 113.

The second gas sensor 101 differs from the gas sensor 1 of the first embodiment in that the third insulating separator 113 is employed in place of the insulating separator 12. In the following description of the second gas sensor 101, structural features similar to those of the gas sensor 1 of the first embodiment will be described by use of reference numerals similar to those of the gas sensor 1, or description thereof will be omitted.

The third insulating separator 113 is a tubular member formed of an insulating material (e.g., alumina) and is held to the inner wall of the sleeve 11 by the tubular metal holding member 73 disposed within the sleeve 11. The third insulating separator 113 includes a tubular separator body portion 113a and a collar portion 113c.

The separator body portion 113a has a terminal disposition hole 113b extending therethrough in the axial direction. Since the separator body portion 113a is similar in structure to the separator body portion 13a of the forward separator 13 of the first embodiment, description thereof is omitted. The terminal disposition hole 113b is similar in structure to the terminal disposition hole 13b of the first embodiment.

As compared with the collar portion 13c of the forward separator 13 of the first embodiment, the collar portion 113c is greater in protruding dimension from the separator body portion 113a (in other words, the outside diameter of a section taken perpendicularly to the axial direction). That is, the collar portion 113c of the third insulating separator 113 is formed in such a manner as to be able to be held between the metal holding member 73 and the inner surface of the sleeve 11. As a result, by means of the collar portion 113c being supported between the metal holding member 73 and the inner surface of the sleeve 11, the position of the third insulating separator 113 disposed within the sleeve 11 is specified.

The third insulating separator 113 having such a structure accommodates a rear end portion (the electrode terminal portions 31, 32, 34, and 35) of the detection element 5 and a plurality of the metal terminals 41 (more specifically, the forward terminal members 43) in the terminal disposition hole 113b, whereby the electrode terminal portions 31, 32, 34, and 35 and a plurality of the metal terminals 41 are electrically connected, respectively.

Similar to the case of the gas sensor 1 of the first embodiment, in the second gas sensor 101 having such a structure, the metal terminal 41 can be divided into the forward terminal member 43 and the rear terminal member 45.

Thus, the second gas sensor 101 having such metal terminals 41 can simultaneously achieve sufficient heat resistance of forward end portions of the metal terminals 41, maintenance of electrical connection between the metal terminals 41 and the detection element 5 (specifically, the electrode terminal members 31, 32, 34, and 35), and maintenance of electrical connection between the metal terminals 41 and the lead wires 37, respectively.

Next, the above embodiments are described while referring to the metal terminal in which the portions of the female connection portion and the male connection portion which come into contact with each other have a sectional shape (a sectional shape taken perpendicularly to the direction of insertion) of a circle or a square; however, the sectional shape is not limited thereto. For example, the female connection portion and the male connection portion may have a sectional shape of a regular polygon, such as a regular pentagon, a regular hexagon, a regular octagon, or a regular dodecagon.

In the above embodiments, the female connection portion and the male connection portion are connected in a divisible manner. However, the female connection portion and the male connection portion may be fixed together by welding, for example.

Material for the forward terminal member and material for the rear terminal member are not limited to the above-mentioned materials. For example, the metal terminal may be composed of the forward terminal member formed of NCF750 and the rear terminal member formed of SUS430; alternatively, the metal terminal may be composed of the forward terminal member formed of SUS631 and the rear terminal member formed of SUS430.

The gas sensor to which the present invention is applied is not limited to an oxygen sensor, but may be a gas sensor for detecting another gas, such as an $NO_x$ sensor or a hydrogen sensor, so long as the gas sensor includes the metal terminals.

DESCRIPTION OF REFERENCE NUMERALS

1: gas sensor; 3: metallic shell; 5: detection element; 11: sleeve; 12: insulating separator; 12a: ventilation path; 13: forward separator; 14: rear separator; 37: lead wire; 37a: core; 41: metal terminal; 43: forward terminal member; 43b: female connection portion; 43e: element contact portion; 43g: diameter-expanding portion; 45: rear terminal member; 45a: signal-wire connection portion; 45b: male connection portion; 45c: diameter-reducing portion; 101: second gas sensor; 112: second insulating separator; 113: third insulating separator; 114: second rear separator; 141: second metal terminal; 143: second forward terminal member; 143b: female connection portion; 143e: element contact portion; 145: second rear terminal member; 145a: signal-wire connection portion; 145b: male connection portion; and 145c: diameter-reducing portion.

The invention claimed is:

1. A gas sensor comprising:
a sensor element having at least one electrode terminal portion through which a detection signal indicative of a result of detection of a target gas is output from the sensor element to external equipment or through which external current or voltage is input to the sensor element;
a metal terminal electrically connected to the electrode terminal portion of the sensor element; and
a signal wire electrically connected to the metal terminal and forming a signal path for outputting the detection signal to the external equipment, wherein
the metal terminal comprises a forward terminal member in contact with the electrode terminal portion, and a rear terminal member connected to the signal wire;
the forward terminal member comprises;
a body portion extending in an axial direction of the gas sensor,
a female connection portion located rearward of the body portion,
a bend portion bent in a direction perpendicular to the axial direction at a forward end of the body portion, and
an element contact portion extended from the bend portion and configured to abut the sensor element,
the rear terminal member comprises;
a male connection portion inserted into the female connection portion, and
a signal wire connection portion crimping the signal wire radially inward;
the forward terminal member and the rear terminal member are configured so that the electrode terminal portion is electrically connected to the signal wire while the male connection portion and the female connection portion are connected together;
the forward terminal member is made of a material superior in heat resistance to and greater in 0.2% yield strength than a material of the rear terminal member;
contact between the sensor element and the element contact portion is maintained through elastic deformation of the bend portion; and
the signal wire connection portion extends from the male connection portion.

2. The gas sensor according to claim 1, wherein the female connection portion and the male connection portion have contacting parts, which come into contact with each other and have a sectional shape of a circle or a regular polygon taken in a direction perpendicular to a direction of insertion.

3. The gas sensor according to claim 2, wherein the rear terminal member is formed such that a forward end portion of the male connection portion reduces in diameter in a forward direction.

4. The gas sensor according to claim 3, wherein the forward terminal member is formed such that a rear end portion of the female connection portion increases in diameter in a rearward direction.

5. The gas sensor according to claim 2, wherein the forward terminal member is formed such that a rear end portion of the female connection portion increases in diameter in a rearward direction.

6. The gas sensor according to claim 1, wherein the rear terminal member is formed such that a forward end portion of the male connection portion reduces in diameter in a forward direction.

7. The gas sensor according to claim 6, wherein the forward terminal member is formed such that a rear end portion of the female connection portion increases in diameter in a rearward direction.

8. The gas sensor according to claim 1, wherein the forward terminal member is formed such that a rear end portion of the female connection portion increases in diameter in a rearward direction.

9. The gas sensor according to claim 1, wherein the sensor element has a shape of a plate.

10. The gas sensor according to claim 1, wherein
the metal terminal comprises at least two forward terminal members, each of which has the element contact portion,
the sensor element contains at least two electrode terminal portions on at least two outer surfaces of the sensor element and
the element contact portion abuts the electrode terminal portion on the outer surface of the sensor element.

11. The gas sensor according to claim 1, wherein the signal wire connection portion extends from the male connection portion in the axial direction.

* * * * *